United States Patent [19]
Blanco et al.

[11] Patent Number: 5,576,204
[45] Date of Patent: Nov. 19, 1996

[54] φ29 DNA POLYMERASE

[75] Inventors: Luis Blanco; Antonio Bernad; Margarita Salas, all of Madrid, Spain

[73] Assignee: Consejo Superior Investigaciones Cientificas, Madrid, Spain

[21] Appl. No.: 10,568

[22] Filed: Feb. 11, 1993

Related U.S. Application Data

[62] Division of Ser. No. 668,945, Mar. 13, 1991, Pat. No. 5,198,543, which is a division of Ser. No. 328,462, Mar. 24, 1989, Pat. No. 5,001,050.

[51] Int. Cl.$^6$ ..................................................... C12N 9/12
[52] U.S. Cl. ............................................................. 435/193
[58] Field of Search ................................................ 435/193

[56] References Cited

U.S. PATENT DOCUMENTS

| | | | |
|---|---|---|---|
| 4,795,699 | 1/1989 | Tabor et al. | 435/5 |
| 5,001,050 | 3/1991 | Blanco et al. | 435/5 |

FOREIGN PATENT DOCUMENTS

| | | |
|---|---|---|
| 9010064 | 9/1990 | WIPO . |
| 9012111 | 10/1990 | WIPO . |
| 9103573 | 3/1991 | WIPO . |

OTHER PUBLICATIONS

PCT Search Report dated Apr. 10, 1994.
Pastrana et al., "Overproduction and purification of protein P6 of Bacillus subtilis phage φ29: role in the initiation of DNA replication," *Nucleic Acids Research*, vol. 13 No. 9 1985 p. 3083.
Watabe et al., "A novel DNA polymerase induced by Bacillus subtilis phage φ29," Nucleic Acids Research, vol. 11. No. 23, 1983, p. 8333.
Zaballos "Initiation of phage φ29 DNA replication by mutants with deletions at the amino end of the terminal protein," *Gene* vol. 63 pp. 113–121, 1988.
Carrascosa et al., "Synthesis in vitro of φ29–Specific Early Proteins Directed by Phage DNA," *Eur. J. Biochem*, 51 (1975), p. 587.
Talavera et al., "Temperature–sensitive Mutants Affected in DNA Synthesis in Phage φ29 of *Bacillus subtilis*," *Eur. J. Biochem*. 31 367, 371 (1972).
Watabe et al., "A 3' to 5' Exonuclease Activity is Associated with Phage φ29 DNA Polymerase," *Biochemical and Biophysical Research Communications*, vol. 123, No. 3. 1984, pp. 1019–1026.
Zaballos et al., "Initiation of phage φ29 DNA replication by mutants with deletions at the carboxyl end of the terminal protein," *Gene*, 43 (1986) 103–110.
Blanco et al., "Cloning and expression of gene 2, required for the protein primed initiation of the *Bacillus subtilis* phage φ29 DNA replication," *Gene*: 29 (1984) 33–40.
Prieto et al., "Interaction of the bacteriophage φ29 protein p6 with double–stranded DNA," Proc. Natl. Acad. Sci., USA vol. 85 pp. 314–318, (1988).
Gutierrez et al., "Signals in the φ29 DNA–Terminal Protein Template for the Initiation of Phage φ29 Replication," *Virology* 155. 474–483 (1986).
Matsumoto et al., "Aphidicolin–Resistant Mutants of Bacteriophage φ29: Genetic Evidence for Altered DNA Polymerase," *Virology* 152 32–38 (1986).
Inciarte et al., "Physical Map of Bacteriophage φ29 DNA," Virology 74, 314–323 (1976).
Kuzmin et al., "S1 plasmid from cms–S–maize mitochondria encodes a viral type DNA–polymerase," *Nucleic Acids Research*, vol. 15 No. 16 1987 p. 6758.
Blanco et al.. "Replication of phage φ29 DNA with purified terminal protein and DNA polymerase. Synthesis of full––length φ29 DNA," *Proc. Natl. Acad. Sci. USA*, vol. 82. pp. 6404–6408 1985.
Salas "A New Mechanism for the Initiation of Replication of φ29 and Adenovirus DNA Priming by the Terminal Protein" Current Topics in Microbiology and Immunology. vol. 109, 1983.
Blanco et al.. "Characterization and purification of a phage φ29 encoded DNA polymerase required for the initiation of replication." *Proc Natl. Acad. Sci. USA*. vol. 81 pp. 5325–5329 1984.
Bernard et al., "Structural and functional relationships between prokaryotic and eukaryotic DNA polymerases," *The EMBO Journal* vol. 6 No. 13 pp. 4219–4225 1987.
Blanco et al. "Effect of Aphidicolin and Nucleotide Analogs on the Phage φ29 DNA Polymerase." *Virology* 153. 179–187 (1986).
Zaballos et al. "A set of expression plasmids for the synthesis of fused and unfused polypeptides in *Escherichia coli*" *Gene* 58 (1987) 67–76.
Blanco et al. "Effect of $NH_{4+}$ Ions on φ29 DNA–Protein p3 Republication. Formation of a Complex between the Terminal Protein and the DNA Polymerase," *Journal of Virology*, 1987 p. 3983 3991. vol. 61 No. 12.
Blanco et al "Characterization of a 3'–5' exonuclease activity in the phage φ29 encoded DNA polymerase" *Nucleic Acids Research* vol. 13 No. 4 1985.
Salas, "Phages with Protein Attached to the DNA Ends"; The Bacteriophages, vol. 1 1988 p. 169.

(List continued on next page.)

*Primary Examiner*—Stephanie W. Zitomer
*Attorney, Agent, or Firm*—Lyon & Lyon

[57] ABSTRACT

An improved method for determining the nucleotide base sequence of a DNA molecule employs a φ-29 type DNA polymerase modified to have reduced or no exonuclease activity. The method includes annealing the DNA molecule with a primer molecule able to hybridize to the DNA molecule; incubating the annealed mixture in a vessel containing four different deoxynucleoside triphosphates, a DNA polymerase, and one or more DNA synthesis terminating agents which terminate DNA synthesis at a specific nucleotide base, wherein each the agent terminates DNA synthesis at a different nucleotide base; and separating the DNA products of the incubating reaction according to size, whereby at least a part of the nucleotide base sequence of the DNA can be determined. The improvement is provision of a DNA polymerase which is a φ29-type DNA polymerase.

6 Claims, 2 Drawing Sheets

OTHER PUBLICATIONS

Barthelemy et al. "Symmetrical transcription in bacteriophage φ29 DNA" Biochimie 70 (1988) 605–609.

Salas et al "Protein primed replication of bacteriophage φ29 DNA," *Biochimica et Biophysica Acta.*, 951 (1988) pp. 419 424.

Blanco et al "Transition from Initiation to Elongation in Protein–Primed φ29 DNA Replication Salt–Dependent Stimulation by the Viral Protein p6." *Journal of Virology* Nov 1988 pp. 4167 4172 vol. 62 No. 11.

Garmendia et al "Site–directed metagenesis in the DNA linking site of bacteriophage φ29 terminal protein isolation and characterization of a $Ser_{232}$ —Thr mutant." *Nucleic Acids Research* vol. 16 No. 13 1988.

Otero et al "Effect of deletions at the amino and carboxyl end on the activity of bacteriophage φ29 protein p6." *Gene Organization and Expression in Bacteriophages*, 1988.

Salas et al., "Protein–primed replication of bacteriophage φ29 DNA", Gene Organization and Expression in Bacteriophages, Salamanca, Spain, Jul. 4–8, 1988.

Hermoso et al., "Interaction of the bacteriophage φ29 protein p6 with double–stranded DNA", Gene Organization and Expression in Bacteriophages, Salamanca, Spain, Jul. 4–8, 1988.

Barthelemy et al., "Characterization of the bacteriophage φ29 protein p4 as a transcriptional activator and location of its DNA recognition site", Gene Organization and Expression in Bacteriophages, Salamanca, Spain, Jul. 4–8, 1988.

Blanco et al., "Processive replication by the bacteriophage φ29 DNA polymerase", Gene Organization and Expression in Bacteriophages, Salamanca, Spain, Jul. 4–8, 1988.

Bernad et al., "Structural and functional analysis of the *Bacillus subtilis* phage φ29 DNA polymerase", Gene Organization and Expression in Bacteriophages, Salamanca, Spain, Jul. 4–8, 1988.

Prieto et al., "Purification in a functional form of the terminal protein of *Bacillus subtilis* phage φ29", Proc. Nat'l. Acad. Sci. USA 81, pp. 1639–1643 (1984).

Garcia et al., "Cloning and expression in *E. coli* of the gene coding for the protein linked to the ends of *Bacillus subtilis* phage φ29 DNA", Gene 21:65–76 (1983).

```
                              EXO 1
               A                      2* *             3                    4
POL 1 (318) PEVTATMISYDNYV-TILDEETLKAWIAK-LEKAPVFA-FDIETDS-L-DNISANLV--GLSFAIEPGMAAMIPVAHDY
SPO2    (1)                         LKTLS-IDIETFSSM-DLLKAGVYAYTEAPDFEILFAYAF-DDDP
T7      (1)                                MIV-SDIEANAL-ESM---TKFHCGM-IMDYSTAEY
T4    (150) NSMYGSVSKWDAKLAAKLDEGGDEVPQEILDRV-IYMPFONERDM-LMEYI
Ø29     (1)                     MKHMP-RKMYS-COFEITTKM-E----DCRMAMGMNIED
PRD1    (1) MPRRSRKKVE-YKIAA-FDFETDPFKHDRI----PKPFSWGFIYNGEI
            3°=>5° EXO

EXO II
               B                      5                D                    *
POL 1 (390) LD-APDQISRERA-ELLKPLI-EDEK----ALKVGQNL--KYDRGILAN-YGTELRGIAFDTMLESYI-LNSVAGRHD
SPO2   (44) VKIIDLAQGDTLPHEVLVAL-TSSK----VIKTAYNAN--FERTCIAKHFNLMI-PAQWRCTAVHAI-TLGLPGMD
T7     (32) VS-YR-PSDFGAYLDALEAEVARGG----LII-VFHGHKYDVPALTKLAKLQI-NRE-FHLPRENCIDTLVL-SRLI
T4    (200)                 NLWEQKRP----AIFTGMNIEG-FDVPYIIMNRVK-MILGE-RSMKRFSPI--GRVKSKLIQNMY
Ø29    (35) HSEYKI----GNSLDEFMAWLKVQA--DL-YFHNL-KFDGAFIINW--LERNGFKWSADGLPNIYNTII--SPMGQWYM
PRD1   (42) YKDYWG----DDCIEQFIYMDTIEEPHVII-YAHNGGKFDFLFLMKYFRGK------KIVNGRI

*
POL 1 (458) MDS------------------------LA-ERW--LKHKTITFEE---IAGKGKNQLT-FN
SPO2  (113) GVAKAKLSA--------QKDKAGK---AL-IRYFSVPCKPTKA---NGQRVRNLPE-HD
T7     (99) HSNLKDTDMG-------L-LRSGKLPGKRFGSHALEAWGYRLGE---MK-GEY-KDDFKRMLEE---QGEEYVDGM-EW
T4    (255) GSKEIYSIDGVSILDYL-DLYKKFAFTNLPSFSLESVAQHET----KK-GKLPYDGPINKLRETNHQRYISYNIIDVES
Ø29   (103) IDICLGYKGKRKIHTVIYQSLKKI-PFFPVKKIAKDFKLTVLKGDIDYHK-ERP---VGYKITPEE---YAY-IKNDIQ-II
PRD1   (96) LEVEHGIHKFR------DSYAILPVPL---AASDEKI--------TREQHKAEI---EIDYGSMERE---LEY-LKGDCV-TL
            E

T4 mutator    Ⓢ PS118        PS131 Ⓓ      Ⓓ Ⓟ      Ⓒ tsme174
                                       PS105 tsme176
```

φ29 DNA POLYMERASE

This is a continuation of application Ser. No. 07/688,945, filed Mar. 13, 1991 issued as U.S. Pat. No. 5,198,543, which is itself a division of application Ser. No. 07/328,462, filed Mar. 24, 1989, now U.S. Pat. No. 5,001,050.

BACKGROUND OF THE INVENTION

This invention relates to DNA polymerases suitable for DNA sequencing.

DNA sequencing involves the generation of four populations of single-stranded DNA fragments, having one defined terminus and one variable terminus. The variable terminus always terminates at a specific given nucleotide base (either guanine (G), adenine (A), thymine (T), or cytosine (C)). The four different sets of fragments are each separated on the basis of their length, on a high resolution polyacrylamide gel; each band on the gel corresponds colinearly to a specific nucleotide in the DNA sequence, thus identifying the positions in the sequence of the given nucleotide base.

Generally there are two methods of DNA sequencing. One method (Maxam and Gilbert sequencing) involves the chemical degradation of isolated DNA fragments, each labeled with a single radiolabel at its defined terminus, each reaction yielding a limited cleavage specifically at one or more of the four bases (G, A, T or C). The other method (dideoxy sequencing) involves the enzymatic synthesis of a DNA strand. Four separate syntheses are run, each reaction being caused to terminate at a specific base (G, A, T or C) via incorporation of the appropriate chain terminating dideoxynucleotide. The latter method is preferred since the DNA fragments are uniformly labelled (instead of end labelled) and thus the larger DNA fragments contain increasingly more radioactivity. Further, $^{35}$S-labelled nucleotides can be used in place of $^{32}$P-labelled nucleotides, resulting in sharper definition; and the reaction products are simple to interpret since each lane corresponds only to either G, A, T or C. The enzymes used for most dideoxy sequencing is the *Escherichia coli* DNA-polymerase I large fragment ("Klenow"), AMV reverse transcriptase, and T7 DNA polymerase (Tabor et al., U.S. Pat. No. 4,795,699). The T7 DNA polymerase used for sequencing is said to be advantageous over other DNA polymerases because it is processive, has no associated exonuclease activity, does not discriminate against nucleotide analog incorporation, and can utilize small oligonucleotides as primers. These properties are said to make the polymerase ideal for DNA sequencing. Id.

SUMMARY OF THE INVENTION

In a first aspect, the invention features an improved method for determining the nucleotide base sequence of a DNA molecule. The method includes annealing the DNA molecule with a primer molecule able to hybridize to the DNA molecule; incubating the annealed mixture in a vessel containing four different deoxynucleoside triphosphates, a DNA polymerase, and one or more DNA synthesis terminating agents which terminate DNA synthesis at a specific nucleotide base, wherein each the agent terminates DNA synthesis at a different nucleotide base; and separating the DNA products of the incubating reaction according to size, whereby at least a part of the nucleotide base sequence of the DNA can be determined. The improvement is provision. of a DNA polymerase which is a φ29-type DNA polymerase.

By φ29-type DNA polymerase is meant any DNA polymerase isolated from the related phages which contain a terminal protein used in the initiation of replication of DNA. These phages are generally described by Salas, 1 The Bacteriophages 169, 1988. These phages are closely related in the structure of their DNA polymerases, some differing by as few as 6 amino acid changes with 5 of those amino acids being replaced by similar amino acids. These phages have a short inverted terminal repeat sequence of length between about 6 and 300 nucleotides. These polymerases have a highly active 3'-5' exonuclease activity, but no 5'-3' exonuclease activity. Surprisingly, although they are related to the T4 family of DNA polymerases, they are able to adequately recognize chain terminating agents such as dideoxynucleosides and therefore are useful for DNA sequencing. This ability is even more surprising since the exonuclease is known to recognize both deoxy and dideoxy ADP. Blanco et al. 13 Nuc. Acid. Res. 1239, 1246, 1985.

In preferred embodiments, the φ29-type DNA polymerase is either that phage polymerase in cells infected with a φ29-type phage: the φ29-type DNA polymerase is chosen from the DNA polymerases of phages: φ29, Cp-1, PRD1, φ15, φ21, PZE, PZA, Nf, M2Y, B103, SFS, GA-1, Cp-5, Cp-7, PR4, PRS, PR722, and L17; or the DNA polymerase is a φ29-type polymerase, modified to have less than ten percent of the exonuclease activity of the naturally-occurring polymerase, most preferably the polymerase has less than one percent, and even more preferably has substantially no exonuclease activity; and the terminating agent is a dideoxynucleotide.

In a related aspect, the invention features a kit for DNA sequencing including a supply of φ29-type DNA polymerase, together with a supply of a chain terminating agent. By kit is meant a container designed to keep these two components separated from each other, preferably in condition for use in a DNA sequencing reaction.

In another related aspect, the invention features a DNA fragment encoding a modified φ29-type DNA polymerase, wherein the polymerase has sufficient DNA polymerase activity for use in DNA sequencing, and an exonuclease activity which is less than 10% the activity of the corresponding naturally occurring φ29-type DNA polymerase.

By corresponding is meant that the modified polymerase is derived from a naturally occurring polymerase, generally by in vitro mutagenesis of the DNA sequence encoding the latter polymerase, and the latter is the corresponding polymerase.

In preferred embodiments, the DNA fragment is modified to substantially eliminate the naturally-occurring exonuclease activity; and the DNA fragment includes a DNA sequence encoding a φ29 DNA polymerase in which the amino acid moiety at position 12, 14, or 16 of the polymerase is replaced by an alanine moiety.

The invention also features a φ29-type DNA polymerase produced from the above described DNA fragments.

In another aspect, the invention features an improved method for amplification of a DNA sequence. The method includes annealing a first and second primer to opposite strands of a double-stranded DNA sequence, and incubating the annealed mixture with a DNA polymerase. The improvement includes employing as the DNA polymerase a φ29-type DNA polymerase.

In preferred embodiments, the first and second primers have their 3' ends directed towards each other after annealing; the method further includes, after the incubation step, denaturing the resulting DNA, annealing the first and second primers to the denatured DNA and incubating the last annealed mixture with the polymerase; the cycle of denaturing, annealing, and incubating is repeated from 10–40 times; the φ29-type DNA polymerase is selected from the DNA polymerases of phages: φ29, Cp-1,-PRD1, φ15, φ21, PZE, PZA, Nf, M2Y, B103, SFS, GA-1, Cp-5, Cp-7, PR4, PR5, PR722, and L17; the DNA polymerase exhibits less than 10% of the naturally-occurring exonuclease activity exhibited by the corresponding naturally-occurring polymerase, most preferably the polymerase has no detectable exonuclease activity.

In a further aspect, the invention features a method for production of DNA molecules of greater than 10 kilobases in length. The method includes providing a template DNA molecule; annealing a primer with the template molecule; and incubating the annealed primer and template molecules in the presence of a φ29-type DNA polymerase, and a mixture of four different deoxynucleoside triphosphates.

The invention also features a method for amplification of a heterologous DNA molecule including covalently bonding a φ29-type terminal DNA sequence at one end of the DNA molecule to form a product; and incubating the product in the presence of a φ29-type DNA polymerase and a terminal protein (see below) of a φ29-type DNA polymerase.

By heterologous is meant any DNA which does not naturally Occur within a φ29-type phage DNA molecule. This includes DNA encoding any desired protein.

A terminal DNA sequence is a sequence which naturally occurs at one or both ends of a φ29-type phage DNA which may be between 6 and 300 bases long. This sequence is specifically recognized and bound by a terminal protein, for example, the p3 protein of φ29.

In preferred embodiments, the method includes providing a φ29-type terminal DNA sequence at each end of the DNA molecule to be amplified; the terminal sequence is provided on a DNA fragment of less than 500 nucleotides: and the terminal protein is the terminal protein of the φ29-type phage in which the φ29-type DNA polymerase naturally occurs.

This invention provides a DNA polymerase which is highly processive, and may be produced with a low exonuclease activity. The high processivity of the polymerase makes it suitable, not only for DNA sequencing, but also for amplification of very large fragments of DNA (in excess of 10 kilobases in length). This makes the polymerase useful in a polymerase chain reaction (PCR)-type procedure or in replicative-type, protein primed, extension reactions. These long lengths of DNA are of use in forensic work, when small samples of DNA are available, and for restriction fragment length polymorphism analysis.

Other features and advantages of the invention will be apparent from the following description of the preferred embodiments thereof, and from the Claims.

DESCRIPTION OF THE PREFERRED EMBODIMENTS

The drawing will first briefly be described.

Figure 2:
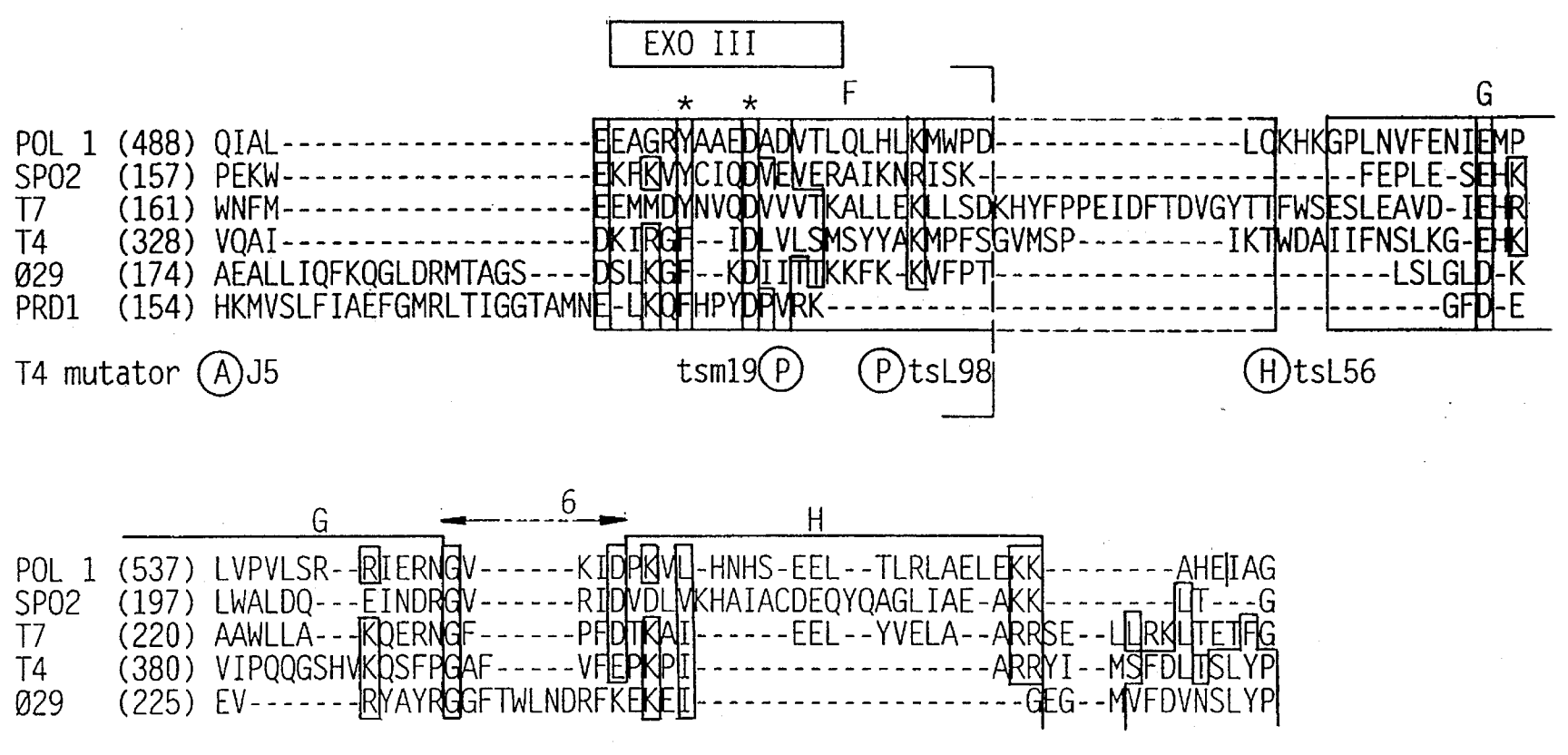

The FIGS. 1 and 2 are a representation of the amino acid sequence of various DNA polymerases showing sites of homology between the polymerases. ExoI, ExoII and ExoIII refer to the three regions of amino acid homology found among the different DNA polymerases compared in the Figure. A steriskts indicate the *E. coli* DNA polymerase I residues involved in either metal binding, or exonucleolytic catalysis. Asterisks indicate the *E. coli* DNA polymerase I residues involved in single-stranded DNA binding. Boxes shown by lines or arrows, and lettered or numbered, are s-helix and β-sheet regions respectively of DNA polymerase I.

DNA Polymerase

In general, a DNA polymerase of this invention is processive. and has naturally-occurring exonuclease activity associated with it. In some preferred embodiments, the DNA polymerase has little or no associated exonuclease activity. These polymerases also have a strand-displacement activity.

By processive is meant that the DNA polymerase is able to continuously incorporate nucleotides using the same primer template, without dissociating from either or both the primer or the template molecules, under conditions normally used for DNA sequencing extension reactions, or other primer extension reactions. Generally, polymerases of the present invention will remain bound to the extended primer or template for at least 1–2 kilobases, generally at least 5 kb–10 kb, under suitable environmental conditions.

The ability of the polymerases of this invention to produce strand displacement is advantageous in this invention because, in combination with high processivity, it allows synthesis of long DNA molecules of at least 70 kb, or even greater. Strand displacement activity is measured by any standard technique, for example, a polymerase may be incubated in a mixture with a single-stranded circular DNA molecule (e.g., M13) and a primer. If DNA molecules of length greater than the original circular molecule are synthesized, then the polymerase is able to displace DNA strands of a double-stranded molecule and continue to synthesize DNA-thus, it has a strand displacement activity. Such activity is generally present in a single protein molecule, e.g., p2 of φ29, and does not require energy in the form of ATP or its equivalent, utilizing only the standard deoxynucleoside triphosphates required to synthesize DNA. This activity is also observed when DNA synthesis is initiated by a terminal protein, e.g., p3 of φ29.

The exonuclease activity associated with DNA polymerases of this invention does not appear to significantly interfere with the use of the polymerase in a DNA sequencing reaction. However, it is preferred that the level of exonuclease activity be reduced to a level which is less than 10% or 1%, preferably less than 0.1% of the activity normally associated with DNA polymerases isolated from cells infected with naturally-occurring bacteriophage.

The DNA polymerases of this invention include polymerases which have been genetically modified to reduce the exonuclease activity of that polymerase, as well as those which are substantially identical to a naturally-occurring φ29-type DNA polymerase or a modified polymerase thereof, or to the equivalent enzymes enumerated above. Each of these enzymes can be modified to have properties similar to those of the φ29 DNA polymerase. It is possible to isolate the enzyme from phage-infected cells directly, but preferably the enzyme is isolated from cells which overproduce it.

By substantially identical is meant that the enzyme may contain amino acid substitutions which do not affect the overall properties of the enzyme. One example of a particularly desirable amino acid substitution is one in which the natural enzyme is modified to remove any exonuclease activity. This modification may be performed by genetic or chemical means.

As an example of this invention we shall describe the use of φ29 DNA polymerase in a variety of useful procedures. This example is not meant to be limiting to the invention;

those skilled in the art will recognize that any of the above enumerated DNA polymerases can be similarly used in the manner described below.

φ29 DNA Polymerase

Bacteriophage φ29 is a linear double-stranded DNA molecule having a protein of 31 kD covalently linked at the 5' end. This terminal protein, termed p3, is the product of viral gene 3, and is linked to The DNA by a phosphoester-bond between the OH group of a serine residue and 5'-dAMP. φ29 replication is initiated at either DNA end by a protein priming mechanism in which a free molecule of the terminal protein p3 reacts with dATP to form a protein-p3-dAMP covalent complex that provides the 3' OH group needed for elongation. The initiation reaction requires, in addition to the gene 3 product and the φ29 DNA-protein p3 template, the product of the viral gene 2 (p2), which is the DNA polymerase. Protein p2 produced from gene 2 has a molecular weight of 66.5 kD. Associated with protein p2 is a 3'-5' exonuclease activity active on single stranded and to some extent on double stranded DNA. Protein p2 may be purified by standard procedure from E0 coli cells harboring a gene 2 containing recombinant plasmid, as described by Blanco et al., 29 Gene 33, 1984. The protein may be further purified by passage over a phosphocellulose column, as described by Blanco et al., 13 Nuc. Acid. Res. 1239, 1985. Blanco et al., id., also describe an exonuclease assay suitable for determination of inactivation of the exonuclease activity by genetic manipulation, as described below. Other enzymes associated with p2 and p3 in bacteriophage φ29 include p5 and p6, which increase the efficiency of polymerization by p2, as described by Salas, 109 Current Topics in Microbiology and Immunology 89, 1983.

Exonuclease Mutants

We shall now briefly describe the cloning of φ29 DNA polymerase and the manipulation of the p2 gene to produce examples of exonuclease mutants useful in this invention.

The starting plasmid was pBw2, which is a pSR322 derivative containing gene 2 of phage φ29, coding for the φ29 DNA polymerase, and including its ribosome-binding sequence (RBS) (Blanco et al. 29 Gene 33, 1984). In this construction the putative ATG initiation codon for the φ29 DNA polymerase is located 30 bp downstream a unique HindIII restriction site. Plasmid pBw2 was linearized with Hind III and subjected to a controlled digestion with the nuclease Bal31. The DNA was then digested with the restriction nuclease ScaI, which cuts 444 base pairs downstream gene 2, and the 5' protruding ends were filled-in with the Klenow fragment of *E. coli* DNA polymerase I. The DNA fragment containing gene 2 was ligated with the T4 DNA ligase to plasmid pAZe3ss (Zaballos et al., 58 Gene 67, 1987) and digested with NcoI, whose 5' protruding ends were then filled-in using Klenow fragment. The ligation product was used to transform competent *E. coli* M72 cells (lysogenic for bacteriophage λ and containing the temperature-sensitive cI857 repressor) and ampicillin-resistant bacteria selected. The latter were replica-plated in plates containing ampicillin (100 μ/ml) by growing them overnight at 30° C., followed by 3 h at 42° C. The colonies were transfered to nitrocellulose filters and lysed with 0.1% sodium dodecyl sulfate. The filters were washed, incubated with rabbit anti-φ29 DNA polymerase serum (produced by standard procedure) and the φ29 DNA polymerase-containing colonies were detected by incubation with [$^{125}$I] protein A followed by autoradiography. DNA sequencing of the selected clones allowed selection of the recombinant plasmids pAZw200 and pAZa203, which include φ29 DNA starting at the ATG triplets corresponding to position 2869–2867 and 2860–2858, respectively, in the open reading frame coding for p2, from the left φ29 DNA end (Yoshikawa et al., 17 Gene, 323, 1982). When the *E. coli* M72 cells, transformed with the recombinant plasmids pAZw200 or pAZa203, containing the gene coding for the φ29 DNA polymerase under the control of the $P_L$ promoter of bacteriophage λ and with the RBS of gene ner of bacteriophage Mu, were grown at 30° C. and then shifted to 42° C. for 20 min to inactivate the λ CI857 repressor, followed by 2 h at 38° C., enzymatically active φ29 DNA polymerase was synthesized. About 150 and 300 μg of highly purified φ29 DNA polymerase was obtained per g of cells transformed with the recombinant plasmids pAZw200 and pAZa203, respectively.

The EcoRI-Hind III fragment from the recombinant plasmid pAZw200, containing the φ29 DNA polymerase gene and the RBS of gene ner of bacteriophage Mu was ligated, using T4 DNA ligase, to the EcoRI-HindIII sites of the replicative form of bacteriophage M13mp19. *E. coli* JM103 cells were transfected with such DNA and white plaques were selected in plates containing X-gal and isopropilthiogalactoside (IPTG). The selected plaques were amplified in liquid medium and the replicative form was isolated to check (by restriction analysis) the presence of the desired EcoRI-HindIII fragment. The single-stranded DNA was also isolated and used for site-directed mutagenesis, carried out as described by Nakamaya et al., 14 Nucl. Acids Res. 9679, 1986. The synthetic oligodeoxynucleotides used for the site-directed mutagenesis were:

1) 5' AGTTGTGCCTTTGAGAC (SEQ. ID. NO:1)

2) 5' GACTTTGCGACAACTAC (SEQ. ID. NO:2)

3) 5' CTCAAATTTGCCGGAGC (SEQ. ID. NO:3)

The recombinant clones containing point mutations were selected by hybridization to the corresponding mutagenic oligonucleotides 5' [$^{32}$P]-labeled with T4 polynucleotide kinase and [$\gamma^{-32}$p] ATP. Single-stranded DNA was isolated from the selected clones and the sequence of the complete DNA polymerase gene was determined to check that each clone contained only the desired mutation. The EcoRI-BstBI fragment from the different clones was ligated with T4 DNA ligase to the same sites of plasmid pABw2, which contains the EcoRI-HindIII fragment of plasmid pAZw200 cloned at the corresponding sites of plasmid pT7-3 of the pT7 series (Tabor et al. 82 Proc. Natl. Acad. Sci. USA, 1074, 1985), under the control of the φ10 promoter of bacteriophage T7. This EcoRI-BstBI fragment replaces the wild-type sequence in that region by the corresponding mutant sequence. In this way, the recombinant plasmids pABn2D12A, pABn2E14A, pABn2D66A, pABn2D12AD66A and pABn2E14AD66A were selected, containing the corresponding amino acid changes from the amino-terminal end of the φ29 DNA polymerase. The recombinant plasmids were used to transform *E. coli* BL21 (DE3) cells containing the bacteriophage T7 RNA polymerase gene in the host DNA under the control of the lac uv5 promoter (Studier et al., 189 J. Mol. Biol. 113, 1986) being, therefore, inducible by IPTG. The ampicillin-resistant bacteria were analyzed for the presence of recombinant plasmids. Expression of the φ29 DNA polymerase mutant proteins was obtained by addition of 1 mM IPTG to *E. coli* cells containing the recombinant plasmids, grown at 37° C. and incubated for 1 h at 37° C. Five different mutant proteins were obtained, with the following amino acid changes: 1) alanine at position 12 (with reference to the first methionine in the gene encoding p2) in place of the natural aspartic acid (D12A); 2) alanine at position 14 instead of glutamic acid (E14A); 3) alanine at position 66 instead of aspartic acid (D66A); 4) alanine at positions 12 and 66 instead of aspartic acid (D12A, D66A); and 5) alanine at position 14 and 66 (E14A, D66A). The different mutant proteins were purified and their 3'-5' exonuclease activity determined by the above standard assay to be 100–1000 fold lower than that of the wild-type naturally occurring φ29 DNA polymerase.

Deposits

Strains pAZW200 (wild type p2 gene), pKC30A1 (wild type p3 gene), pABN2D12AD66A (exonuclease deficient p2 gene having alanine at positions 12 and 66) have been deposited on Mar. 24, 1989, with the American Type Culture Collection, 12301 Parklawn Drive, Rockville, Md. 20852 and assigned numbers 67918, 67919, 67920 respectively.

Applicants' and their assignees, Spanish Research Council (Consejo Superior De Investigaciones Scientificas, Serrano No. 117, 28006, Madrid, SPAIN), acknowledge their responsibility to replace these cultures should they die before the end of the term of a patent issued hereon, 5 years after the last request for a culture, or 30 years, whichever is the longer, and its responsibility to notify the depository of the issuance of such a patent, at which time the deposits will be made irrevocably available to the public. Until that time the deposits will be made available to the Commissioner of Patents under the terms of 37 CFR Section 1–14 and 35 USC Section 112.

Referring to the Figure, the oligonucleotides used to form the above mutants were selected by taxing into account the amino acid sequence homology with other polymerases and those mutations known to reduce exonuclease activity of DNA polymerase I. Derbyshire et al. 240 Science 199, 1988. Other mutations which are likely to produce suitable exonuclease mutants are shown in the black boxes. Generally, the amino acid at these portions is either deleted or replaced with a different amino acid. Large deletions or multiple replacement of amino acids are also useful in this invention. After mutagenesis, the level of exonuclease activity is measured and the amount of DNA polymerase activity determined to ensure it is sufficient for use in this invention (e.g., for DNA sequencing), being processive and having strand displacement activity.

Uses

DNA polymerases of this invention are useful in the following methods:

Filling in the 3' recessed termini created by digestion of DNA with restriction enzymes; labelling the termini of DNA fragments with protruding 5' ends (filling in reaction); labelling the termini of blunt-ended DNA fragments or DNA fragments with protruding 3' termini (exchange reaction); removing the 3' protruding termini of DNA fragments; labelling DNA fragments for use as hybridization probes by partial digestion of double-stranded DNA using the naturally associated 3'-5' exonuclease activity, followed by a filling reaction with labelled dNTPs (displacement reaction); synthesis of long (over 5–10 kb) as well as short single-stranded DNA probes containing multiple copies of a desired sequence, obtained by strand-displacement synthesis on single stranded DNA, such long probes may be labelled with labelled dNTPS at a high specific activity; random labelling of double-stranded DNA at a high specific activity by using degenerated oligonucleotide primers; second-strand cDNA synthesis in cDNA cloning; sequencing DNA using a Sanger-type dideoxy system (Sanger et al. 74 Proc. Natl. Acad. Sci. USA 5463, 1977) on single- and double-stranded DNA templates; sequencing DNA by a plus/minus-type method (Sanger et al., 94 J. Mol. Biol. 441, 1975); random mutagenesis of single- and double-stranded DNA templates by using an exonuclease-deficient DNA polymerase under conditions of low DNA replication fidelity; site-directed mutagenesis on double stranded DNA templates; gene amplification or synthesis of long double-stranded DNA fragments using synthetic oligonucleotides as primers; and amplification or synthesis of double-stranded DNA fragments using a φ29-type DNA replication system including a φ29-type DNA polymerase, a terminal protein, any accessory proteins necessary to enhance the reaction, and a φ29-type DNA-protein p3 template.

The φ29-type DNA polymerases are particularly useful for DNA sequencing, performing a polymerase chain reaction, and for amplification without the need for temperature cycling to produce extremely long strands of DNA. These methods will now be discussed in detail.

EXAMPLE 1

P.C.R.

There follows an example of a polymerase chain reaction using φ29 DNA polymerase. In general, the DNA polymerase may simply be used in place of Klenow or Taq polymerases.

0.1 pmol of target DNA are mixed with 300 pmol each of selected oligonucleotides (15–20 mers), and 75 nmol of each deoxynucleoside triphosphate (1N5 mM) in 50 µl of a buffer containing 50 mM Tris-HCl (pH 7.5) and 10 mM magnesium chloride. The solution is brought to 5° C. for 10 minutes, and cooled to 30° C. for 1 min in a waterbath. 1 µcontaining 20 ng of φ29 DNA polymerase (either wild type or an exonuclease mutant) is added to the mixture and the reaction allowed to proceed for 5 min at 30° C., after which the cycle of heating, cooling, adding enzyme, and reacting is repeated about nine times. The polymerase used is purified by standard procedures.

Prior polymerases used in polymerase chain reactions failed to provide DNA fragments in the size range greater than about 2 kilobases (Saiki et al., 239 Science 487, 1988; Keohavong et al., 71 Gene 211, 1988). This relative short size is probably due to the secondary structure and hinderance produced by reannealing of the DNA fragment, which impedes the progress of these DNA polymerases. Because φ29 DNA polymerase has a high processivity and strand displacement ability, it is an ideal enzyme for DNA amplification to produce long amplified molecules.

EXAMPLE 2

DNA Sequencing

For DNA sequencing, the sequence procedure using single-stranded DNA as a template was essentially as described by Tabor et al., 84 Proc. Natl. Acad. Sci. USA 4767, 1987 with some modification.

In the annealing reaction, the annealing reaction mixture (20 µl) contained 2.5 µg of template DNA, 60 ng of primer (a 10-fold molar ratio to the template) in a buffer containing 40 mM Tris-HCl, pH 7.5, 10 mM $MgCl_2$ and 75 mM NaCl. The mixture was heated to 65° C. for 15 min and then cooled to room temperature (20°–25° C.) over 30 min.

In the labelling reaction, a single labelling reaction was used for all four termination reactions. To the annealing mixture (20 µl) was added 20 µl of a mixture containing 0.6 µM each dGTP, dTTP, dCTP and [$\alpha$-$^{32}$P]dATP, 2 mM dithiothreitol, 100 mM Tris-HCl pH 7.5, 20 mM $MgCl_2$ and 8% glycerol. Labelling was started by addition of the φ29 DNA polymerase (either wild type or exonuclease deficient, 150 ng). Incubation was at room temperature for 5 min, at which time the reaction was complete. Four aliquots (8 μl each) of the "labelling" reaction mixture were used for the "termination" reactions.

In the extension-termination reaction, four separate dideoxy "termination" mixtures were prepared in 1.0 ml microcentrifuge tubes. Each mixture (2 μl) contained 20 μM each of the three dNTPs, the remaining dNTP, and its corresponding dideoxy- NTP, being at 2 μM and 200 μM, respectively. Eight microliters of the above labelling reaction mixture was added to each termination mixture and incubated for 15 min at 30° C. Three microliters of stop solution (95% formamide/20 mM EDTA/0.05% xylene cyanol/0.05% bromophenol blue) was then added. The mixtures were heated at 95° C. for 2 min immediately prior to loading 6 μl onto a sequencing gel.

A protocol for double-stranded DNA sequence is similar to the above protocol but preceded by an alkali-denaturation step.

For the reasons discussed above, the secondary structure of the DNA template may impede the progress of DNA polymerases. This may occur either at an pallindromic sequence, which may form a hairpin structure, or at other sequences where an enzyme pauses dependent upon a specific sequence. Because of the high processivity and strand displacement ability of ϕ29 DNA polymerases, the sequencing results obtained with this polymerase are superior to those of the prior art.

In the following methods it is useful to include accessory proteins, such as p5 and p6 in the reaction mix. Preparation of p6 is described by Blanco et al., 62 J. Virol. 4167, 1988. Preparation of p5 was as follows:

*E. coli* K12ΔH1Δtrp cells carrying the gene 5-containing recombinant plasmid pGM26 or *B. subtilis* cells infected with the phage ϕ29 mutant sus 14(1242) were used as a source of protein p5 for purification. The protein p5 present in the *E. coli* extracts amounted to ~1.4% of the total protein after 2.5 h of induction at 42° C., and that present in the *B. subtilis* extracts was ~2.7% of the total protein.

Ten g of *E. coli* K12AH1Atrp cells harboring the gene 5-containing recombinant plasmid pGM26, were induced for 2.5 h at 42° C., were ground with alumina (20 g) and extracted with buffer A (50 mM Tris-HCl pH 7.5 5% glycerol) containing 0.3 M KCl. The lysate was centrifuged for 10 min at 16,500×g and the pellet reextracted with the same buffer. The two supernatants were pooled and precipitated with ammonium sulfate to 65% saturation. The pellet was dissolved in buffer A, dialyzed against the same buffer, diluted with buffer A +20% glycerol and passed through a DEAE- cellulose column (2.7 cm×10 cm) equilibrated with buffer A+10 mM NaCl. The column was washed first with buffer A+20% glycerol, then with buffer A, and protein p5 was finally eluted with buffer A+50 mM NaCl. The fractions containing protein p5 were pooled and precipitated with ammonium sulfate to 65% saturation. The pellet was resuspended in 1.2 ml of buffer A+1.4M ammonium sulfate and 50% glycerol. The pellet remaining after centrifugation, containing most of protein p5, was dissolved in buffer A+50% glycerol. Protein p5, was purified by a similar procedure from *B. subtilis* cells infected with the ϕ29 delayed lysis mutant sus14(1242). In all purification steps protein p5 was followed by SDS-polyacrylamide gel electrophoresis.

In some preparations, after the last purification step, protein p5 was centrifuged for 24 h at 260,000×g at 0° C. in a 5 ml 15 to 30% (v/v) glycerol gradient in 50 mM Tris-HCl, pH 7.5, 0.2M NaCl. After centrifugation, 0.2 ml fractions were collected and the presence of protein p5 was determined.

EXAMPLE 3

Replicative-type Amplification

As described above, long strands of DNA may be synthesized by primer elongation using a ϕ29-type DNA polymerase. This property may be used to amplify DNA without the need for the temperature cycling used in prior polymerase chain reactions. This process makes use of a protein primer rather than an oligonucleotide primer. Generally, the terminal repeat sequences of a ϕ29-type DNA polymerase are covalently bonded by any of a number of standard methods, to each end of the DNA molecule to be amplified. This bonding may be by direct ligation of the sequence to be amplified, or may be by a procedure similar to site-directed mutagenesis, where an oligonucleotide comprising the terminal sequence is constructed to allow recombination of that nucleotide sequence to adjacent DNA which is required to be amplified. In an alterntive method, a restriction endonuclease may be used to randomly cut genomic DNA and synthetic oligonucleotides, comprising the terminal sequences, placed at these sites. In each case the DNA is amplified by provision of p2 and p3 proteins, along with nucleoside triphosphates. An example of this now follows:

A preparation of ϕ29 DNA protein-p3 isolated by standard procedure is cut with the restriction nuclease ClaI to produce two fragments of length 6147 and 13138 bp. A DNA fragment containing an appropriate multicloning site is then ligated to join the two ClaI fragments. The DNA fragment to be amplified is then ligated to one of the multicloning sites and the resulting DNA is used as a template for DNA synthesis.

The incubation mixture contains, in 25 pl, 50 mM Tris-HCl, pH 7.5, 10 mM dithiothreitol, 1 mM spermidine, 20 mM ammonium sulfate, 80 μM each dCTP, dGTP, dTTP and [α-$^{32}$P]dATP, 80 ng of ϕ29 DNA polymerase, 20 ng of terminal protein p3 purified as described (Prieto et al. 81 Proc. Natl. Acad. Sci. USA, 1639, 1984) from *E. coli* N99λts cells harboring the gene 3-containing recombinant plasmid pKC30Al (Garcia et al., 21Gene 65, 1983), proteins p5 (9 μg) and p6 (2 μg) purified from ϕ29-infected *B. subtilis* as described above, and the desired amount of template (10 ng-1 μg). After incubation for 60 min. at 30° C., 25 μl containing all the components of the system except the template are added and the mixture is incubated again for 60 min. at 30° C. (2nd cycle). The cycles are repeated in the same way several times.

EXAMPLE 4

Synthesis of Long Strands of DNA

The DNA polymerases of this invention permit ready synthesis of very long DNA molecules useful in a large number of applications, e.g., RFLP analysis, and DNA probe construction. There follows an example of this methodology.

Single-stranded M13 DNA was hybridized with a 17-mer M13 oligonucleotide primer. The incubation mixture contained, in 10 μl, 50 mM Tris-HCl pH 7.5, 10 mM MgCl$_2$, 1 mM DTT, 0.5 μg of primed M13 DNA, 80 μM each dCTP, dGTP, dTTP and [α-$^{32}$p] dATP and ϕ29 DNA polymerase (50 ng). After incubation for 40 min at 30° C. the samples were filtered through Sephadex G-S0 spin columns in the presence of 0.1% sodium dodecyl sulfate and the Cerenkov radiation of the excluded fraction was counted. To analyze the size of the DNA synthesized, a sample was subjected to electrophoresis in alkaline 0.7% agarose gels along with DNA length markers. The DNA markers were detected with ethidium bromide and the synthesized DNA was detected by autoradiography of the dried gel. In 40 min of incubation at 30° C., DNA longer than 70 Kb was synthesized.

Other embodiments are within the following claims.

We claim:

1. A Φ29-type DNA polymerase produced from a non-naturally occurring DNA fragment consisting of DNA encoding a modified Φ29-type DNA polymerase, wherein said polymerase comprises sufficient DNA polymerase activity for use in DNA sequencing, and an exonuclease activity which is less than 10% the activity of the corresponding naturally occurring Φ29-type DNA polymerase.

2. The φ29-type DNA polymerase of claim 1, wherein said DNA encoding a modified φ29-type DNA polymerase encodes a DNA polymerase having no exonuclease activity.

3. The φ29-type DNA polymerase of claim 1, wherein said φ29-type DNA polymerase is that polymerase present in cells infected with the phage φ29.

4. The φ29-type DNA polymerase of claim 2, wherein said φ29-type DNA polymerase is that polymerase present in cells infected with the phage φ29.

5. The φ29-type DNA polymerase of claim 1, wherein said phage is selected from one of the group consisting of φ29, Cp-1, PRD1, φ15, φ21, PZE, PZA, Nf, M2Y, B103, SF5, GA-1, Cp-5, Cp-7, PR4, PR5, PR722, and L17.

6. The φ29-type DNA polymerase of claim 2, wherein said phage is selected from one of the group consisting of φ29, Cp-1, PRD1, φ15, φ21, PZE, PZA, Nf, M2Y, B103, SF5, GA-1, Cp-5, Cp-7, PR4, PR5, PR722, and L17.

* * * * *

SEQUENCE LISTING ( 1 ) GENERAL INFORMATION:

( i i i ) NUMBER OF SEQUENCES: 3

( 2 ) INFORMATION FOR SEQ ID NO: 1:

( i ) SEQUENCE CHARACTERISTICS:
        ( A ) LENGTH: 17
        ( B ) TYPE: nucleic acid
        ( C ) STRANDEDNESS: single
        ( D ) TOPOLOGY: linear ( i i ) SEQUENCE DESCRIPTION: SEQ ID NO: 1:

AGTTGTGCCT TTGAGAC    17

( 2 ) INFORMATION FOR SEQ ID NO: 2:

( i ) SEQUENCE CHARACTERISTICS:
        ( A ) LENGTH: 17
        ( B ) TYPE: nucleic acid
        ( C ) STRANDEDNESS: single
        ( D ) TOPOLOGY: linear ( i i ) SEQUENCE DESCRIPTION: SEQ ID NO: 2:

GACTTTGCGA CAACTAC    17

( 2 ) INFORMATION FOR SEQ ID NO: 3:

( i ) SEQUENCE CHARACTERISTICS:
        ( A ) LENGTH: 17
        ( B ) TYPE: nucleic acid
        ( C ) STRANDEDNESS: single
        ( D ) TOPOLOGY: linear ( i i ) SEQUENCE DESCRIPTION: SEQ ID NO: 3:

CTCAAATTTG CCGGAGC    17